United States Patent [19]

Schäfer et al.

[11] Patent Number: 5,661,109

[45] Date of Patent: Aug. 26, 1997

[54] ANELLATED (OXA)HYDANTOINS AND THEIR USE AS HERBICIDES

[75] Inventors: Matthias Schäfer, Goldbach; Helmut Baier, Wehrheim; Karlheinz Drauz, Freigericht; Hans-Peter Krimmer, Frankfurt; Sabine Landmann, Gelnhausen, all of Germany

[73] Assignee: DEGUSSA Aktiengesellschaft, Frankfurt am Main, Germany

[21] Appl. No.: 374,782

[22] PCT Filed: Jul. 29, 1993

[86] PCT No.: PCT/EP93/02026

§ 371 Date: Apr. 21, 1995

§ 102(e) Date: Apr. 21, 1995

[87] PCT Pub. No.: WO94/03458

PCT Pub. Date: Feb. 17, 1994

[30] Foreign Application Priority Data

Jul. 30, 1992 [DE] Germany .................. 42 25 167.2

[51] Int. Cl.$^6$ .................. A01N 43/90; C07D 498/04
[52] U.S. Cl. .................. 504/270; 504/193; 504/196; 548/110; 548/113; 548/218
[58] Field of Search .................. 548/218, 110, 548/113; 504/270, 193, 196

[56] References Cited

U.S. PATENT DOCUMENTS 5,068,341  11/1991  Poetsch et al. .................. 548/154

*Primary Examiner*—Patricia L. Morris
*Attorney, Agent, or Firm*—Cushman Darby & Cushman IP Group of Pillsbury Madison & Sutro LLP

[57] ABSTRACT

The invention relates to new anellated (oxa) hydantoins, and herbicidal compositions containing same. The invention also relates to methods for controlling noxious plants using the anellated (oxa) hydantoins of the invention.

6 Claims, No Drawings

ANELLATED (OXA)HYDANTOINS AND THEIR USE AS HERBICIDES

The present invention relates to new anellated (oxa) hydantoins of the formula I

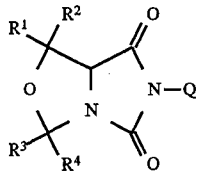

wherein $R^1$ to $R^4$ and Q have the meaning given in the description, a method for their preparation and their use as herbicides.

As has already been communicated, certain thiohydantoins (see EP-A2 0 290 902) or heterocyclic imides (see EP-A1 272 594, EP-B10 070 389) can be used as herbicides.

Surprisingly, new bicyclic imides have now been found which possess a distinctly better herbicidal action and excellent selectivity.

The present invention therefore comprises compounds of the formula I

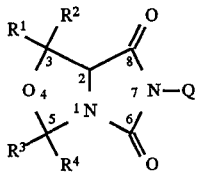

wherein $R^1$ and $R^2$, independently of one another, represent hydrogen or a group of the series $(C_1-C_4)$ alkyl, $(C_1-C_2)$ haloalkyl or phenyl, which is optionally fluorine-substituted, $R^3$ and $R^4$, independently of one another, represent hydrogen, $(C_1-C_4)$ alkyl, phenyl, both optionally fluorine-substituted, and/or chlorine-, bromine- or methyl-substituted, $(C_1-C_4)$ alkoxy; or also together form a carbocyclic ring which may optionally be $(C_1-C_4)$ alkyl-substituted, Q represents one of the radicals $Q_1-Q_7$

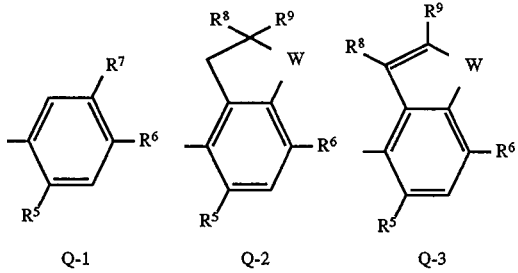

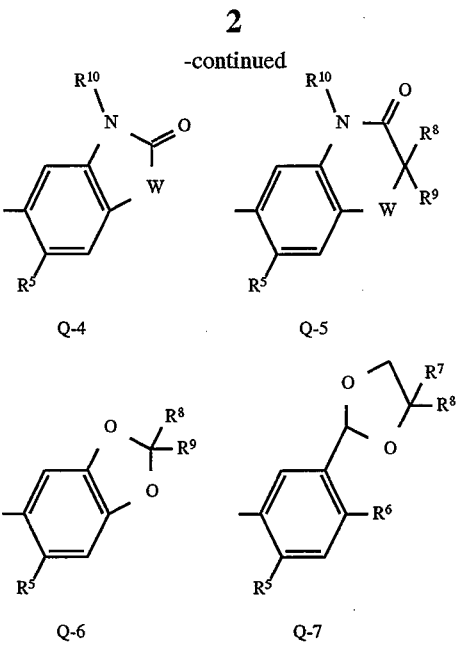

wherein

W represents O or S, $R^5$ represents hydrogen or halogen, $R^6$ represents $(C_1-C_2)$ alkyl, $(C_1-C_2)$ haloalkyl, $OCH_3$, $SCH_3$, $OCHF_2$, halogen, CN Or $NO_2$, $R^7$ represents hydrogen, $(C_1-C_8)$ alkyl, $(C_1-C_8)$ haloalkyl, halogen, $OR^{11}$, $S(O)_nR^{11}$, $COR^{11}$, $CO_2R^{11}$, $C(O)SR^{11}$, $C(O)NR^{12}R^{13}$, CHO, $CH=CHCO_2R^{11}$, $CO_2N=CR^{14}R^{15}$, $NO_2$, CN, $NHSO_2R^{16}$ or $NHSO_2NHR^{16}$, $R^8$ represents hydrogen, $(C_1-C_3)$ alkyl, $(C_1-C_3)$ haloalkyl or halogen, $R^9$ represents hydrogen, $(C_1-C_3)$ alkyl, $(C_1-C_3)$ haloalkyl or halogen; or if Q is Q-2 or Q-6, $R^8$ and $R^9$ together with the carbon atom to which they are bonded can be C=O;

$R^{10}$ represents $(C_1-C_6)$ alkyl, $(C_1-C_6)$ haloalkyl, $(C_2-C_6)$ alkoxyalkyl, $(C_3-C_6)$ alkenyl or $(C_3-C_6)$ alkynyl, $R^{11}$ represents $(C_1-C_8)$ alkyl, $(C_3-C_8)$ cycloalkyl, $(C_3-C_8)$ alkenyl, $(C_3-C_8)$ alkynyl, $(C_1-C_8)$ haloalkyl, $(C_2-C_8)$ alkoxyalkyl, $(C_2-C_8)$ alkylthioalkyl, $(C_2-C_8)$ alkylsulphinyl alkyl, $(C_2-C_8)$ alkylsulphonylalkyl, $(C_3-C_8)$ alkoxyalkoxyalkyl, $(C_4-C_8)$ cycloalkylalkyl, $(C_2-C_4)$ carboxyalkyl, $(C_3$ $C_8)$ alkoxycarbonylalkyl, $(C_6-C_8)$ alkenyloxycarbonylalkyl, $(C_6-C_8)$ alkynyloxycarbonylalkyl, $(C_4-C_8)$ alkenoxyalkyl, $(C_6-C_8)$ cycloalkoxyalkyl, $(C_4-C_8)$ alkynyloxyalkyl, $(C_3-C_8)$ haloalkoxyalkyl, $(C_4-C_8)$ haloalkenyloxyalkyl, $(C_4-C_8)$ haloalkynyloxyalkyl, $(C_6-C_8)$ cycloalkylthioalkyl, $(C_4-C_8)$ alkenylthioalkyl, $(C_4$ $C_8)$ alkynylthioalkyl, $(C_1-C_4)$ alkyl-substituted with phenoxy or benzyloxy, which may both optionally be halogen-, $(C_1-C_3)$ alkyl- or $(C_1-C_3)$ haloalkyl-substituted; $(C_4-C_8)$ trialkylsilylalkyl, $(C_3-C_8)$ cyanoalkyl, $(C_3-C_8)$ halocycloalkyl, $(C_3-C_8)$ haloalkenyl, $(C_5-C_8)$ alkoxyalkenyl, $(C_8-C_8)$ haloalkoxyalkenyl, $(C_5-C_8)$ alkylthioalkenyl, $(C_3-C_8)$ haloalkynyl, $(C_5-C_8)$ alkoxyalkynyl, $(C_5-C_8)$ haloalkoxyalkynyl, $(C_5-C_8)$ alkylthioalkynyl, $(C_2-C_8)$ alkylcarbonyl, benzyl optionally substituted with halogen, $(C_1-C_3)$ alkyl or $(C_1-C_3)$ haloalkyl; $CHR^{17}COR^{18}$, $CHR^{17}P(O)(OR^{18})_2$, $P(O)(OR^{18})_2$, CHR$^{17}$P(S)(OR$^{18}$)$_2$, CHR$^{17}$C(O)NR$^{12}$R$^{13}$, CHR$^{17}$C(O)NH$_2$, phenyl or pyridyl, both optionally substituted with halogen, (C$_1$-C$_3$) alkyl, (C$_1$-C$_3$) haloalkyl or (C$_1$-C$_4$) alkoxy, R$^{12}$ and R$^{14}$, independently of one another, represent hydrogen or (C$_1$-C$_4$) alkyl, R$^{13}$ and R$^{15}$, independently of one another, represent (C$_1$-C$_4$) alkyl, phenyl, optionally substituted with halogen, (C$_1$-C$_3$) alkyl, (C$_1$-C$_3$) haloalkyl or (C$_1$-C$_4$) alkoxy, or R$^{12}$ and R$^{13}$ may be combined into rings as —(CH$_2$)$_5$—, —(CH$_2$)$_4$—, or —CH$_2$CH$_2$OCH$_2$CH$_2$—, wherein one or more H atoms in each ring may be substituted optionally by (C$_1$-C$_3$) alkyl, phenyl or benzyl;

R$^{14}$ and R$^{15}$ together with the carbon atom to which they are bonded can form a (C$_3$-C$_8$) cycloalkyl group, R$^{16}$ represents (C$_1$-C$_4$) alkyl or (C$_1$-C$_4$) haloalkyl, R$^{17}$ represents hydrogen or (C$_1$-C$_3$) alkyl, R$^{18}$ represents (C$_1$-C$_6$) alkyl, (C$_3$-C$_6$) alkenyl or (C$_3$-C$_6$) alkynyl, and n represents 0, 1, 2.

In the definitions given above, the term "alkyl", alone or in the compound term as "alkylthio" or "haloalkyl", includes a linear or branched chain, for example, methyl, ethyl, n-propyl, isopropyl or the various butyl isomers. Alkoxy includes methoxy, ethoxy, n-propyloxy, isopropyloxy- and the different butyl isomers. Alkenyl includes linear or branched alkenes, for example, 1-propenyl, 2-propenyl, 3-propenyl and the different butyl isomers. Cycloalkyl includes cyclopropyl, cyclobutyl, cyclopentyl and cyclohexyl. The term "halogen", alone or in the compounds term as "haloalkyl" signifies fluorine, chlorine, bromine or iodine. In addition, when "haloalkyl" is used in the compound term, then "alkyl" maybe partially or wholly substituted by halogen atoms, which in their turn may be identical or different. Examples of haloalkyl include CH$_2$CH$_2$F, CF$_2$CF$_3$ and CH$_2$CHFCl.

The following radicals are preferred, wherein

R$^1$ and R$^2$, independently of one another, represent hydrogen or a group of the series (C$_1$-C$_4$) alkyl, (C$_1$-C$_2$) haloalkyl or phenyl, which is optionally fluorine-substituted, R$^3$ and R$^4$, independently of one another, represent hydrogen, (C$_1$-C$_3$) alkyl, phenyl, optionally fluorine-substituted and/or chlorine-, bromine-, methyl-substituted, (C$_1$-C$_2$) alkoxy; or together form a carbocyclic ring which may optionally be (C$_1$-C$_2$) alkyl-substituted, Q signifies

Q-1  Q-2  Q-3

Q-4  Q-5

Q-6  Q-7 wherein

W represents O or S, n represents 0, 1, 2,

R$^5$ represents hydrogen or halogen,

R$^6$ represents halogen or CN,

R$^7$ represents hydrogen, (C$_1$-C$_4$) alkyl, (C$_1$-C$_4$) haloalkyl, halogen, OR$^{11}$, S(O)$_n$R$^{11}$, COR$^{11}$, CO$_2$R$^{11}$, C(O)SR$^{11}$, C(O)NR$^{12}$R$^{13}$, CH=CHCO$_2$R$^{11}$, CO$_2$N=CR$^{14}$R$^{15}$, NHSO$_2$R$^{16}$ or NHSO$_2$NHR$^{16}$, R$^8$ represents hydrogen, (C$_1$-C$_3$) alkyl or (C$_1$-C$_3$) haloalkyl, R$^9$ represents hydrogen, (C$_1$-C$_3$) alkyl or (C$_1$-C$_3$) haloalkyl; or if Q is Q-2 or Q-6, R$^8$ and R$^9$ together with the carbon atom to which they are bonded can be C=O;

R$^{10}$ represents (C$_1$-C$_4$) alkyl, (C$_1$-C$_4$) haloalkyl, (C$_2$-C$_4$) alkoxyalkyl, (C$_3$-C$_6$) alkenyl or (C$_3$-C$_6$) alkynyl, R$^{11}$ represents (C$_1$-C$_4$) alkyl, (C$_3$-C$_6$) cycloalkyl, (C$_3$-C$_6$) alkenyl, (C$_3$-C$_6$) alkynyl, (C$_1$-C$_4$) haloalkyl, (C$_2$-C$_4$) alkoxyalkyl, (C$_2$-C$_4$) alkylthioalkyl, (C$_2$-C$_4$) alkylsulphinylalkyl, (C$_2$-C$_4$) alkylsulphonylalkyl, (C$_3$-C$_6$) alkoxyalkoxyalkyl, (C$_4$-C$_8$) cycloalkylalkyl, (C$_2$-C$_4$) carboxyalkyl, (C$_3$-C$_6$) alkoxycarbonylalkyl, (C$_6$-C$_8$) alkenyloxycarbonylalkyl, (C$_6$-C$_8$) alkynyloxycarbonylalkyl, (C$_4$-C$_6$) alkenoxyalkyl, (C$_6$-C$_8$) cycloalkoxyalkyl, (C$_4$-C$_6$) alkynyloxyalkyl, (C$_3$-C$_6$) haloalkoxyalkyl, (C$_4$-C$_8$) haloalkenyloxyalkyl, (C$_4$-C$_6$) haloalkynyloxyalkyl, (C$_6$-C$_8$) cycloalkylthioalkyl, (C$_4$-C$_6$) alkenylthioalkyl, (C$_4$-C$_6$) alkynylthioalkyl, (C$_1$-C$_2$) alkyl-substituted with phenoxy or benzyloxy, which may both optionally be halogen-, (C$_1$-C$_3$) alkyl- or (C$_1$-C$_3$) haloalkyl-substituted; (C$_4$-C$_8$) trialkylsilylalkyl, (C$_3$-C$_4$) cyanoalkyl, (C$_3$-C$_6$) halocycloalkyl, (C$_3$-C$_6$) haloalkenyl, (C$_5$-C$_6$) haloalkoxyalkenyl, (C$_5$-C$_6$) alkylthioalkenyl, (C$_3$-C$_6$) haloalkynyl, (C$_5$-C$_6$) alkoxyalkynyl, (C$_5$-C$_6$) haloalkoxyalkynyl, (C$_5$-C$_6$) alkylthioalkynyl, (C$_2$-C$_4$) alkylcarbonyl, benzyl optionally substituted with halogen, (C$_1$-C$_2$) alkyl or (C$_1$-C$_2$) haloalkyl; CHR$^{17}$COR$^{18}$ CHR$^{17}$P(O)(OR$^{18}$)$_2$, P(O)(OR$^{18}$)$_2$, CHR$^{17}$P(S)(OR$^{18}$)$_2$, CHR$^{17}$C(O)NR$^{12}$R$^{13}$, CHR$^{17}$C(O)NH$_2$, phenyl or pyridyl, both optionally substituted with halogen, ($C_1$–$C_3$) alkyl, ($C_1$–$C_3$) haloalkyl or ($C_1$–$C_4$) alkoxy, $R^{12}$ and $R^{14}$, independently of one another, represent hydrogen or ($C_1$–$C_2$) alkyl, $R^{13}$ and $R^{15}$, independently of one another, represent ($C_1$–$C_2$) alkyl, phenyl, optionally substituted with halogen, ($C_1$–$C_2$) alkyl, ($C_1$–$C_2$) haloalkyl or ($C_1$–$C_2$) alkoxy, or $R^{12}$ and $R^{13}$ may be combined into rings as —($CH_2$)$_5$—, —($CH_2$)$_4$—, or —$CH_2CH_2OCH_2CH_2$—, wherein one or more H atoms in each ring may be substituted optionally by ($C_1$–$C_2$) alkyl, phenyl or benzyl;

$R^{14}$ and $R^{15}$ together with the carbon atom to which they are bonded can form a ($C_3$–$C_6$) cycloalkyl group, $R^{16}$ represents ($C_1$–$C_4$) alkyl or ($C_1$–$C_4$) haloalkyl, $R^{17}$ represents hydrogen or ($C_1$–$C_3$) alkyl, $R^{18}$ represents ($C_1$–$C_4$) alkyl, ($C_3$–$C_4$) alkenyl or ($C_3$–$C_4$) alkynyl.

The following radicals are preferred, wherein $R^1$ and $R^2$, independently of one another, represent hydrogen or a group of the series ($C_1$–$C_3$) alkyl, ($C_1$–$C_2$) haloalkyl or phenyl, which is optionally fluorine-substituted, $R^3$ and $R^4$, independently of one another, represent hydrogen, ($C_1$–$C_3$) alkyl, or also together form a 5- to 6-membered carbocyclic ring, which may optionally substituted with ($C_1$–$C_4$) alkyl radicals, Q signifies

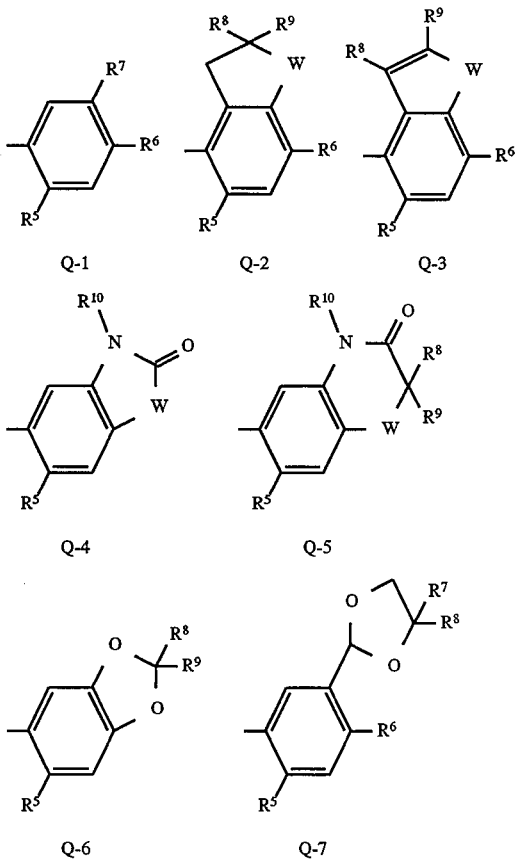

Q-1  Q-2  Q-3
Q-4  Q-5
Q-6  Q-7 wherein
W represents O or S,
n represents 0, 1, or 2, $R^5$ represents hydrogen, fluorine or chlorine, $R^6$ represents chlorine, bromine or cyanogen, $R^7$ represents hydrogen, $OR^{11}$ or $CO_2R^{11}$, $R^8$ and $R^9$, independently of one another, represent hydrogen, ($C_1$–$C_2$) alkyl or ($C_1$–$C_2$) haloalkyl, $R^{10}$ represents ($C_1$–$C_2$) alkyl, ($C_1$–$C_2$) haloalkyl, ($C_3$–$C_4$) alkenyl or ($C_3$–$C_4$) alkynyl, $R^{11}$ represents ($C_1$–$C_4$) alkyl, ($C_3$–$C_6$) cycloalkyl, ($C_3$–$C_6$) alkenyl, ($C_3$–$C_6$) alkynyl, ($C_1$–$C_4$) haloalkyl, ($C_2$–$C_4$) alkoxyalkyl, ($C_2$–$C_4$) alkylthioalkyl, ($C_2$–$C_4$) alkylsulphinylalkyl, ($C_2$–$C_4$) alkylsulphonylalkyl, ($C_3$–$C_6$) alkoxyalkoxyalkyl, ($C_4$–$C_8$) cycloalkylalkyl, ($C_2$–$C_4$) carboxyalkyl, ($C_3$–$C_6$) alkoxycarbonylalkyl, ($C_6$–$C_8$) alkenyloxycarbonylalkyl, ($C_6$–$C_8$) alkynyloxycarbonylalkyl, ($C_6$–$C_8$) cycloalkoxyalkyl, ($C_4$–$C_6$) alkenyloxyalkyl, ($C_4$–$C_6$) alkynyloxyalkyl, ($C_3$–$C_6$) haloalkoxyalkyl, ($C_4$–$C_8$) haloalkenyloxyalkyl, ($C_4$–$C_6$) haloalkynyloxyalkyl, ($C_6$–$C_8$) cycloalkylthioalkyl, ($C_4$–$C_6$) alkenylthioalkyl, ($C_4$–$C_6$) alkynylthioalkyl, ($C_1$–$C_2$) alkyl-substituted with phenoxy or benzyloxy, which are both optionally substituted with halogen-, ($C_1$–$C_3$) alkyl- or ($C_1$–$C_3$) haloalkyl; ($C_4$–$C_8$) trialkylsilylalkyl, ($C_3$–$C_4$) cyanoalkyl, ($C_3$–$C_6$) halocycloalkyl, ($C_3$–$C_6$) haloalkenyl, ($C_5$–$C_6$) alkoxyalkenyl, ($C_5$–$C_6$) haloalkoxyalkenyl, ($C_8$–$C_6$) alkylthioalkenyl, ($C_3$–$C_6$) haloalkynyl, ($C_5$–$C_6$) alkoxyalkynyl, ($C_5$–$C_6$) haloalkoxyalkynyl, ($C_5$ $C_6$) alkylthioalkynyl, ($C_2$–$C_4$) alkylcarbonyl, benzyl optionally substituted with halogen, ($C_1$–$C_2$) alkyl or ($C_1$–$C_2$) haloalkyl; $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl or pyridyl, both optionally substituted with fluorine, chlorine or bromine, ($C_1$–$C_2$) haloalkyl or ($C_1$–$C_2$) alkoxy, $R^{12}$ represents hydrogen or ($C_1$–$C_2$) alkyl, or $R^{13}$ represents ($C_1$–$C_2$) alkyl, phenyl optionally substituted with fluorine, chlorine, bromine, ($C_1$–$C_2$) alkyl, ($C_1$–$C_2$) haloalkyl or ($C_1$–$C_2$) alkoxy, or $R^{12}$ and $R^{13}$ may be combined into rings as —($CH_2$)$_5$—, —($CH_2$)$_4$—, or —$CH_2CH_2OCH_2CH_2$—, wherein one or more H atoms in each ring may be substituted optionally by ($C_1$–$C_2$) alkyl, $R^{17}$ represents hydrogen or ($C_1$–$C_2$) alkyl, $R^{18}$ represents ($C_1$–$C_2$) alkyl, ($C_3$–$C_4$) alkenyl or ($C_3$–$C_4$) alkynyl.

The following radicals are preferred, wherein $R^1$ and $R^2$, independently of one another, represent hydrogen, ($C_1$–$C_3$) alkyl, ($C_1$–$C_2$) haloalkyl or phenyl, $R^3$ and $R^4$, independently of one another, represent hydrogen or ($C_1$–$C_3$) alkyl, or together form a 5- to 6-membered carbocyclic ring.

Q signifies

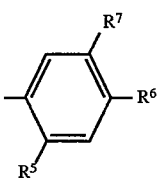

Q-1 wherein $R^5$ represents fluorine or chlorine, $R^6$ represents chlorine, $R^7$ represents $OR^{11}$ or $CO_2R^{11}$, $R^{11}$ represents $(C_1-C_4)$ alkyl, $(C_3-C_6)$ cycloalkyl, $(C_3-C_6)$ alkenyl, $(C_3-C_4)$ alkynyl, $(C_1-C_3)$ haloalkyl, $(C_2-C_4)$ alkoxyalkyl, $(C_3-C_6)$ alkoxycarbonylalkyl, $(C_6-C_8)$ alkenyloxycarbonylalkyl or $(C_6-C_8)$ alkynyloxycarbonyl.

The present invention relates both to the possible individual stereoisomers of the formula I and to mixtures of the isomers. The stereoisomers having the 2R,3S configuration are preferred to others.

The new anellated (oxa)hydantoins of the general formula I are obtained according to the present invention by a general method A, when aryl isocyanates of the general formula II

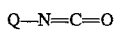

wherein

Q has the meaning given above, and oxazolidine carboxylic acid (ester) of the general formula III

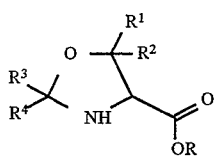

wherein $R^1$, $R^2$, $R^3$ and $R^4$ ($R^3=R^4\ne H$) have the meaning given above and R is H, $(C_1-C_4)$ alkyl or an active ester, are reacted together according to method A optionally in the presence of an acid acceptor and optionally in the presence of a diluent.

The invention also provides a method B for preparing compounds of the formula I, which is illustrated below, and wherein $R^1$ to $R^4$ and Q have the above, meanings, wherein a compound of the formula III, wherein R stands for H and

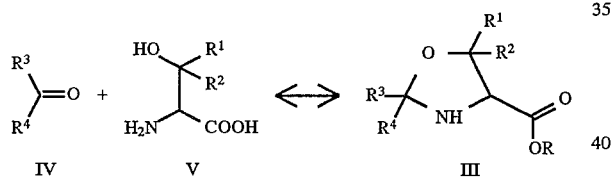

which can be prepared under equilibrium conditions from compounds of the formula IV and compounds of the formula V or salts thereof optionally in the presence of an acid acceptor and optionally in the presence of a diluent, is reacted with a compound of the formula II optionally in the presence of an acid acceptor and optionally in the presence of a diluent, in order to obtain compounds of the formula VI, wherein R is H, $(C_1-C_4)$ alkyl or an active ester

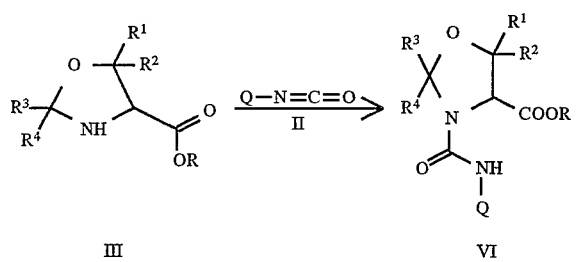

which can then be converted by ring closure into compounds of the formula I.

The invention also provides a method C for preparing compounds of the formula I, which is illustrated below, and wherein $R^1$ to $R^4$ have the above meanings. To this end a compound of the formula III, wherein R stands for H or $(C_1-C_4)$ alkyl, is reacted with phosgene or a phosgene substitute, with first of all compounds of the formula VII being formed, which latter compounds are then reacted with compounds of the formula VIII, wherein Q has the meaning given above, in order to obtain compounds of the formula VI,

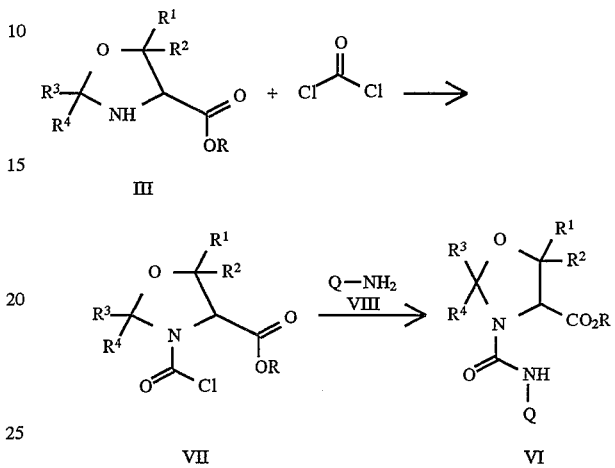

which can then be converted by ring closure into compounds of the formula I.

The invention also provides a method D for preparing compounds of the formula I, which is illustrated below, and wherein $R^1$ to $R^4$ and Q have the above meanings, wherein a compound of the formula II is reacted with a compound of the formula IX, optionally in the presence of an acid acceptor and optionally in the presence of a diluent, in order to obtain compounds of the formula X, and the compounds X thus obtained

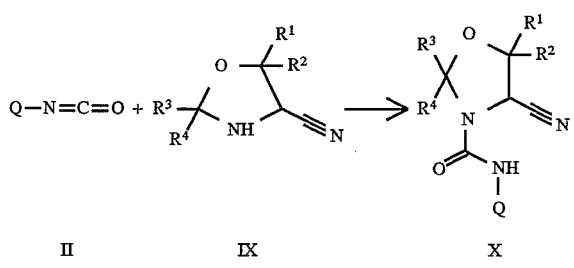

are then hydrolysed and converted by ring closure into compounds of the formula I.

The present invention also provides a method E for preparing compounds of the formula I, wherein the compounds of the formula XI

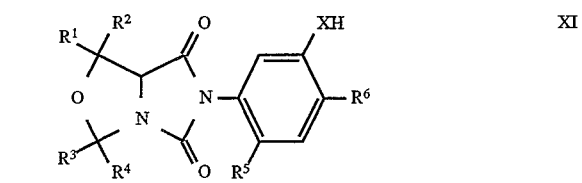

wherein $R^1$ to $R^6$ have the meanings given above and X signifies O, S or NH, are reacted with a halide of the formulae XII, XIII or XIV, $$R^{11}-Z \qquad \text{XII}$$

$$R^{16}SO_2-Z \qquad \text{XIII}$$

$$R^{16}NHSO_2-Z \qquad \text{XIV}$$

wherein Z is an atom of chlorine, bromine or iodine and $R^{11}$ and $R^{16}$ have the meanings given above.

Finally it has been found that the new anellated (oxa) hydantoins of the general formula I possess outstanding herbicidal properties.

In the method A, in the case where R represents alkyl, the reaction is conducted in an inert organic solvent, for example, in an aromatic solvent such as toluene, chlorobenzene; a halogenated hydrocarbon such as chloroform or methylene chloride; an ether such as diisopropyl ether; or in acetonitrile or dimethylformamide, optionally base-catalysed at temperatures of between 20° and 120° C. Preferably organic bases are used, for example, organic amines such as triethylamine or pyridine (see EP-A1 0 272 594). Variants of the general method A are described in EP-A2 0 070 389.

In the method B, which has proved successful particularly in cases where $R^3$ and $R^4$ represent H, the reaction proceeds in water as solvent or, preferably, in the two-phase system water/organic solvent. Particularly preferred is the method of operation whereby compounds of the formulae IV and V, optionally salts of V, are added to an inorganic base, for example, an alkali metal hydroxide or alkaline earth metal hydroxide, carbonate or hydrogen carbonate such as sodium hydroxide or potassium carbonate, or to an organic base, for example, an organic amine such as trieethylamine, and then maintained for several days, preferably 3 to 10 h, at a temperature of between −40° and +50° C., preferably between −10° and +10° C.

The compound of the formula III is formed in this aqueous solution in equilibrium. To it the isocyanate of the formula II, dissolved in an inert organic solvent, for example, toluene, chlorobenzene or chloroform, is added dropwise with vigorous stirring.

The pH-value of the aqueous phase is then established at between 1 and 3 by means of acid, preferably an inorganic acid such as aqueous hydrochloric acid or sulphuric acid. The urea derivatives of the formula VI thus arising are then formed into rings by known methods at a temperature of between 50° and 100° C. or, optionally, by conversion into an ester (R stands for alkyl or active ester) (see Houben-Weyl, Methoden der Organischen Chemie, volume XXV/1 and XXV/2 (1974)).

The compounds of the formula II are known or can be prepared analogously by known methods; see Houben-Weyl, Methoden der Organischen Chemie, volume VIII, page 120 (1952); Houben-Weyl, volume IX, pages 875, 869 (1955); EP-B1 0 070 389; U.S. Pat. No. 4,881,967; EP-A1 322 401; U.S. Pat. No. 3,495,967; EP-A2 300 307; EP-A2 349 832.

Amines of the formula III are known and for $R^3=R^4\neq H$ can be prepared analogously to known methods see, for example, D. Seebach et al., Helv. Chim. Acta, volume 70, 1194 (1987).

Amines of the general formula IX are known or can be prepared according to EP-A 3 073 569 or in a manner analogous to the methods described there.

The present invention also relates to the use of the compounds of the formula I as herbicides as well as herbicidal compositions which contain an effective content of a compound of the formula I and a carrier. Carriers are preferably surface-active substances, solid or liquid diluents.

The invention also relates to a method for controlling noxious plants, wherein a herbicidally effective quantity of a compound according to formula I is applied to the noxious plants or to their environment (prior to or after germination).

CHEMICAL EXAMPLES

Example 1

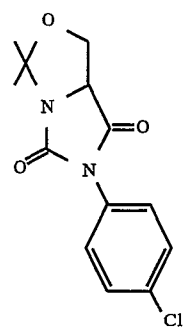

A mixture of 2,2-dimethyloxazolidine-4-carboxylic methyl ester (1.99 g, 0.01 mol), triethylamine (50.0 mg, 0.5 mmol) and toluene (30 ml) is prepared, to which 4-chlorophenyl isocyanate (1.40 g, 0.009 mol) dissolved in 20 ml of toluene is added dropwise. The reaction mixture is stirred at 20° C. for 15 h and then washed with 10% aqueous hydrochloric acid (3×10 ml) and water (3×10 ml), dried over sodium sulphate and filtered. After concentrating the filtrate by evaporation, the residue is dissolved in diethyl ether and reprecipitated from petroleum ether.

2.28 g (81% of the theoretical quantity) of 7-(4-chlorophenyl)-5,5-dimethyl-6,8-dioxo-4-oxa-1,7-diazabicyclo[3.3.0]octane having a melting point of 97°–98° C. is obtained.

Example 2

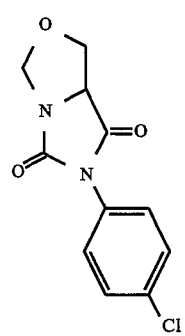

A mixture of serine (1.05 g, 0.01 mol), 37% aqueous formaldehyde solution (2 g) and aqueous sodium hydroxide solution (10 ml) is maintained at 4° C. for 12 h, cooled to 0° C., then 4-chlorophenyl isocyanate (1.55 g) dissolved in chlorobenzene (5 ml) is added dropwise. The reaction mixture is then stirred at 0°–5° C. for ½ h and at room temperature for approximately 2 h, the aqueous phase is extracted by shaking with chloroform (3×10 ml) and the collected organic phases are discarded.

The aqueous phase is then acidified to pH 1 with 5% aqueous hydrochloric acid and the product is introduced into the organic phase by shaking with ethyl acetate (3×10 ml), dried over sodium sulphate and filtered. After concentrating the filtrate by evaporation, the residue is taken up in acetonitrile (25 ml) and reacted with N-hydroxysuccinimide (1.15 g, 0.01 mol). N,N'-dicyclohexyl carbodiimide (2.06 g, 0.01 mol), dissolved in acetonitrile (15 ml), is then added dropwise at 20° C. The reaction mixture is stirred for 12 h under reflux, then filtered and the filtrate is concentrated by evaporation. The remaining residue is taken up in a little acetone and again precipitated with water.

7-(4-chlorophenyl)-6,8-dioxo-4-oxa-1,7-diazabicyclo[3.3.0]octane having a melting point of between 74° to 76° C. is obtained in a quantity of 1.75 g (74% of the theoretical quantity).

The compounds of the general formula I shown in the following tables can be prepared analogously to Examples 1 and 2 and in accordance with the general description of methods A to E according to the present invention.

TABLE 1

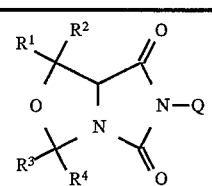

| $R^1$ | $R^2$ | $R^3$ | $R^4$ | $R^5$ | $R^6$ | $R^7$ | Melting point °C. |
|---|---|---|---|---|---|---|---|
| H | H | $nC_3H_7$ | $CH_3$ | H | Cl | H | 88–94 |
| H | H | $C_2H_5$ | $C_2H_5$ | H | Cl | H | 112–114 |
| H | H | $C(CH_3)_3$ | H | H | Cl | H | 112–114 |
| H | H | $C_6H_5$ | $CH_3$ | H | Cl | H | 138–139 |
| H | H | $-(CH_2)_4-$ | — | H | Cl | H | 127–128 |
| H | H | $-(CH_2)_5-$ | — | H | Cl | H | 141–141.5 |
| H | H | $-(CH_2)_5-$ | — | H | Br | H | |
| H | H | $-(CH_2)_5-$ | — | Cl | Cl | H | |
| H | H | $-(CH_2)_6-$ | — | H | Cl | H | 87–89 |
| H | H | $-(CH_2)_5-$ | — | F | Cl | H | |
| H | H | $-(CH_2)_5-$ | — | F | Cl | $CO_2CH(CH_3)_2$ | glass-like |
| H | H | $CH_3$ | $CH_3$ | F | Cl | $CO_2CH(CH_3)_2$ | glass-like |
| H | $CH_3$ | $-(CH_2)_5-$ | — | H | Cl | H | 95–97 |
| H | H | H | H | Cl | Cl | H | |
| H | H | H | H | H | Cl | H | 74–76 |
| H | H | H | H | Cl | Cl | Cl | |
| H | H | H | H | F | Cl | $CO_2CH(CH_3)_2$ | 89–91 (1 isomer) |
| H | H | H | H | F | Cl | $CO_2CH(CH_3)_2$ | Resin (2 isomer) |
| H | $CH_3$ | H | H | F | Cl | $CO_2CH(CH_3)_2$ | glass-like (1 isomer) |
| H | $CH_3$ | H | H | F | Cl | $CO_2CH(CH_3)_2$ | Resin (2 isomer) |
| H | $CH_3$ | H | H | H | Cl | H | 96–98 |
| H | H | H | H | F | Cl | $OCH_3$ | 172–175 |
| H | H | H | H | F | Cl | $OCH(CH_3)_2$ | glass-like |
| H | $CH_3$ | H | H | F | Cl | $OCH(CH_3)_2$ | glass-like |
| H | $CH_3$ | H | H | F | Cl | $OCH_2C\equiv CH$ | glass-like |
| H | $C_6H_5$ | H | H | F | Cl | $CO_2CH(CH_3)_2$ | 119–121 |
| H | $CH_3$ | H | H | F | Cl | $OCH_2CO_2CH_3$ | glass-like |
| H | $CH_3$ | H | H | F | Cl | $O(CH_2)_2OC_2H_5$ | glass-like |
| H | $CH_3$ | H | H | F | Cl | $OCH(CH_3)C\equiv CH$ | glass-like |
| H | $CH_3$ | H | H | F | Cl | $OCH_2CH=CH_2$ | |
| H | $CH_3$ | H | H | F | Br | OEt | |
| H | $CH_3$ | H | H | F | Cl | $OCH_2CH_2CH_3$ | |
| H | $CH_3$ | H | H | F | Cl | $OCH(CH_3)CO_2CH_3$ | |
| H | $CH_3$ | H | H | Cl | Cl | $OCH_2C\equiv CH$ | |
| H | $CH_3$ | H | H | F | Cl | $OCH_2CO_2CH_2C\equiv CH$ | |
| H | $CH_3$ | H | H | F | Cl | $OCH_2CO_2CH_2C\equiv CH$ | |
| H | $CH_3$ | H | H | F | Cl | $OCH_2CO_2C_5H_{11}$ | |
| H | $CH_3$ | H | H | F | Cl | CN | |
| H | $CH_3$ | H | H | F | Cl | $OCH(CH_3)C\equiv CH$ | |
| H | $CH_3$ | H | H | F | Cl | $OSi(CH_3)_3$ | |
| H | $CH_3$ | H | H | F | Cl | $SCH_3$ | |
| H | $CH_3$ | H | H | F | Cl | $SCH(CH_3)_2$ | |
| H | $CH_3$ | H | H | F | Cl | $SCH_2CH=CH_2$ | |
| H | $CH_3$ | H | H | F | Cl | $SCH_2C\equiv CH$ | |
| H | $CH_3$ | H | H | F | Cl | $SCH_2CO_2C_5H_{11}$ | |

TABLE 1-continued

Structure: R¹R² on carbon, with O, N-Q, N, R³R⁴ forming a ring with two C=O groups.

Q = phenyl with R⁵ (ortho), R⁶ (para), R⁷ (meta)

| R¹ | R² | R³ | R⁴ | R⁵ | R⁶ | R⁷ | Melting point °C. |
|---|---|---|---|---|---|---|---|
| H | CH₃ | H | H | F | Cl | OCH₂CON(CH₃)(OCH₃) | |
| H | CH₃ | H | H | F | Cl | OC(CH₃)=N—OCH₃ | |
| H | CH₃ | H | H | F | Cl | OCH₂CH=N—OCH₃ | |
| H | CH₃ | H | H | F | Cl | CO₂CH(CH₃)₂ | Resin (3 isomer) |
| H | CH₃ | H | H | F | Cl | OCH₂CH=N—OCH₂CH=CH₂ | |
| H | CH₃ | H | H | F | Cl | OCH₂CH=N—OCH₂CO₂CH₃ | |
| H | CH₃ | H | H | F | Cl | SCH₂CO₂H | |
| H | CH₃ | H | H | F | Cl | SCH₂CO₂CH₂C≡CH | |
| H | CH₃ | H | H | F | Cl | SCH₂CO₂CH₃ | |
| H | CH₃ | H | H | F | Cl | OCH₂CH(cyclopropyl with 2 Cl) | |
| H | CH₃ | H | H | F | Cl | OCHF₂ | |
| H | CH₃ | H | H | F | Cl | OCH₂C(Cl)=CH₂ | |
| H | CH₃ | H | H | F | Cl | OCH₂CH=CHCl | |
| H | CH₃ | H | H | F | Cl | OCF₂CHF₂ | |
| H | CH₃ | H | H | Cl | Cl | NHSO₂Me | |
| H | CH₃ | H | H | Cl | Cl | NHSO₂CH(CH₃)₂ | |
| H | CH₃ | H | H | H | CH₃ | OCH₂CH=CH₂ | |
| H | CH₃ | H | H | H | CH₃ | OCH₂C≡CH | |
| H | CH₃ | H | H | F | CH₃ | OCH₂C≡CH | |
| H | CH₃ | H | H | F | CH₃ | OCH(CH₃)C≡CH | |
| H | CH₃ | H | H | F | Cl | NO₂ | |
| H | CH₃ | H | H | F | CN | OCH(CH₃)C≡CH | |
| H | CH₃ | H | H | H | CN | OCH₂C≡CH | |
| H | CH₃ | H | H | Cl | Cl | NHSO₂NHCH₃ | |
| H | CH₃ | H | H | F | Cl | CO₂CH₂CH₃ | |
| H | CH₃ | H | H | F | Cl | CO₂CH(CH₃)CF₃ | |
| H | CH₃ | H | H | F | Cl | CO₂CH₂CH₂CH₃ | |
| H | CH₃ | H | H | F | Cl | CO₂CH(CH₃)CH₂CH₃ | |
| H | CH₃ | H | H | F | Cl | CO₂CH(CH₃)C≡CH | |
| H | CH₃ | H | H | F | Cl | CO₂N(CH₃)₂ | |
| H | CH₃ | H | H | F | Cl | CO₂—N(morpholino) | |
| H | CH₃ | H | H | F | Cl | CO₂CH(CH₃)CH₂SCH₃ | |
| H | CH₃ | H | H | F | Cl | CO₂CH(CH₃)CO₂CH₂CH₃ | |
| H | CH₃ | H | H | F | Cl | CO₂CH₂CF₃ | |
| H | CH₃ | H | H | F | Cl | OCH₂C(O)CH₃ | |
| H | CH₃ | H | H | F | Cl | OCH₂P(O)(OC₂H₅)₂ | |
| H | CH₃ | H | H | F | Cl | OCH₂P(S)(OC₂H₅)₂ | |
| H | CH₃ | H | H | F | Cl | OCH₂C(O)N(CH₃)₂ | |
| H | CH₃ | H | H | F | Cl | OCH₂C(O)N(morpholino) | |

TABLE 1-continued

[Structure: R¹R²C(O-)(CR³R⁴-N(C(=O))-C(=O)-N-Q with Q = phenyl ring bearing R⁵, R⁶, R⁷]

| R¹ | R² | R³ | R⁴ | R⁵ | R⁶ | R⁷ | Melting point °C. |
|---|---|---|---|---|---|---|---|
| H | CH₃ | H | H | F | Cl | OCH₂C(O)NH₂ | |
| H | C₆H₅ | H | H | F | Cl | CO₂CH(CH₃)₂ | |
| H | C₆H₅ | H | H | H | Cl | H | |
| H | C₂H₅ | H | H | F | Cl | CO₂CH(CH₃)₂ | |
| H | C₂H₅ | H | H | F | Cl | OCH₂C≡CH | |
| H | C₂H₅ | H | H | F | Cl | OCH(CH₃)C≡CH | |
| H | CH(CH₃)₂ | H | H | F | Cl | CO₂CH(CH₃)₂ | |
| H | CF₃ | H | H | F | Cl | CO₂CH(CH₃)₂ | |
| H | CF₃ | H | H | F | Cl | OCH₂C≡CH | |
| H | CF₃ | H | H | F | Cl | OCH(CH₃)C≡CH | |
| H | C₆H₄F | H | H | F | Cl | CO₂CH(CH₃)₂ | |
| H | CH₃ | H | H | F | CN | CO₂CH(CH₃)₂ | |
| H | CH₃ | H | H | F | Cl | CH=CHCO₂CH₂CH₃ | |

TABLE 2

[Structure with Q = phenyl ring bearing R⁵, R⁶ and a -CH(R⁸)(R⁹)W substituent]

| R¹ | R² | R³ | R⁴ | R⁵ | R⁶ | R⁸ | R⁹ | W | Melting point °C. |
|---|---|---|---|---|---|---|---|---|---|
| H | H | CH₃ | CH₃ | F | Cl | H | H | O | |
| H | H | CH₃ | CH₃ | F | Cl | H | CH₃ | O | |
| H | H | —(CH₂)₅— | — | F | Cl | H | CH₃ | O | |
| H | H | H | H | F | Cl | H | H | O | |
| H | H | H | H | F | Cl | H | CH₃ | O | |
| H | H | H | H | F | Cl | CH₃ | CH₃ | O | |
| H | H | H | H | F | Cl | CH₃ | CH₂CH₃ | O | |
| H | H | H | H | F | Cl | CH₃ | CH₂F | O | |
| H | H | H | H | F | Cl | H | CH₃ | S | |
| H | CF₃ | H | H | F | Cl | H | CH₃ | O | |
| H | CH₃ | H | H | F | Cl | H | H | O | |
| H | CH₃ | H | H | Cl | Cl | H | H | O | |
| H | CH₃ | H | H | H | Cl | H | CH₃ | O | |
| H | CH₃ | H | H | Cl | Cl | H | CH₃ | O | |
| H | CH₃ | H | H | Cl | Cl | CH₃ | CH₃ | O | |
| H | CH₃ | H | H | F | Cl | H | CH₃ | O | |
| H | CH₃ | H | H | F | Cl | CH₃ | CH₃ | O | |
| H | CH₃ | H | H | F | Br | CH₃ | CH₃ | O | |
| H | CH₃ | H | H | F | CH₃ | H | CH₃ | O | |
| H | CH₃ | H | H | F | CH₃ | CH₃ | CH₃ | O | |
| H | CH₃ | H | H | F | OCH₃ | H | CH₃ | O | |
| H | CH₃ | H | H | F | CN | H | CH₃ | O | |
| H | CH₃ | H | H | F | CF₃ | H | CH₃ | O | |
| H | CH₃ | H | H | H | OCF₂H | H | CH₃ | O | |
| H | CH₃ | H | H | F | OCF₂H | H | CH₃ | O | |
| H | CH₃ | H | H | F | Cl | CH₃ | CH₂CH₃ | O | |
| H | CH₃ | H | H | F | Cl | H | CH₂CH₃ | O | |
| H | CH₃ | H | H | F | Cl | H | CH₂Br | | |
| H | CH₃ | H | H | F | Cl | H | CH₂F | O | |
| H | CH₃ | H | H | F | Cl | H | CH₂Cl | O | |

TABLE 2-continued

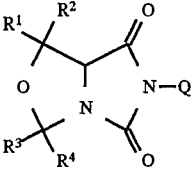

| R¹ | R² | R³ | R⁴ | R⁵ | R⁶ | R⁸ | R⁹ | W | Melting point °C. |
|---|---|---|---|---|---|---|---|---|---|
| H | CH₃ | H | H | F | Cl | H | CH₂(CH₂)₂F | O | |
| H | CH₃ | H | H | F | Cl | H | CH₂CH₂Cl | O | |
| H | CH₃ | H | H | F | Cl | H | CH(CH₃)F | O | |
| H | CH₃ | H | H | F | Cl | H | CH(CH₃)₂ | O | |
| H | CH₃ | H | H | F | Cl | H | CH₂(CH₂)₃Br | O | |
| H | CH₃ | H | H | F | Br | H | CH₂CH₃ | O | |
| H | CH₃ | H | H | F | Br | H | CH₂Br | O | |
| H | CH₃ | CH₃ | CH₃ | F | Cl | H | CH₃ | O | |

TABLE 3

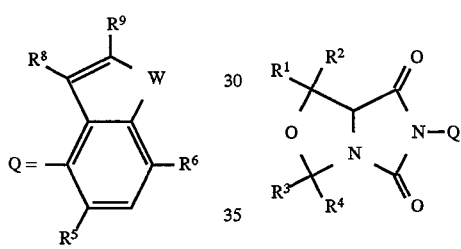

| R¹ | R² | R³ | R⁴ | R⁵ | R⁶ | R⁸ | R⁹ | W | Melting point °C. |
|---|---|---|---|---|---|---|---|---|---|
| H | H | H | H | H | H | H | Cl | S | |
| H | H | H | H | F | Cl | H | H | S | |
| H | H | H | H | F | Cl | H | Cl | S | |
| H | H | H | H | F | Cl | CH₃ | CH₃ | S | |
| H | H | H | H | F | Cl | H | H | O | |
| H | H | H | H | F | Cl | H | Cl | O | |
| H | H | CH₃ | CH₃ | F | Cl | H | H | S | |
| H | H | CH₃ | CH₃ | F | Cl | H | Cl | S | |
| H | CH₃ | H | H | H | H | H | H | S | |
| H | CH₃ | H | H | H | SCH₃ | H | H | S | |
| H | CH₃ | H | H | H | H | H | Cl | S | |
| H | CH₃ | H | H | H | H | Cl | Cl | S | |
| H | CH₃ | H | H | H | H | H | CH₂CH₃ | S | |
| H | CH₃ | H | H | Cl | Cl | H | CH₃ | S | |
| H | CH₃ | H | H | F | Cl | H | CH₃ | S | |
| H | CH₃ | H | H | F | Cl | CH₃ | CH₃ | S | |
| H | CH₃ | H | H | Cl | Cl | H | CH₃ | O | |
| H | CH₃ | H | H | F | Cl | H | CH₃ | O | |
| H | CH₃ | H | H | F | Cl | CH₃ | CH₃ | O | |
| H | CH₃ | CH₃ | CH₃ | F | Cl | H | Cl | S | |

TABLE 4

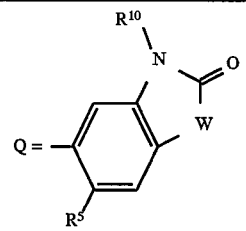

| R¹ | R² | R³ | R⁴ | R⁵ | R¹⁰ | W | Melting point °C. |
|---|---|---|---|---|---|---|---|
| H | H | H | H | F | H | S | |
| H | H | H | H | F | CH₃ | S | |
| H | H | H | H | F | CH₂CH₃ | S | |
| H | H | H | H | F | CH₂C≡CH | S | |
| H | H | H | H | F | CH(CH₃)C≡CH | S | |
| H | H | H | H | F | CH₂CH=CH₂ | S | |
| H | H | H | H | F | CH₂C≡CH | O | |
| H | CH₃ | H | H | Cl | H | S | |
| H | CH₃ | H | H | F | H | S | |
| H | CH₃ | H | H | F | CH₃ | S | |
| H | CH₃ | H | H | F | CH₂CH₃ | S | |
| H | CH₃ | H | H | F | CH₂C≡CH | S | |
| H | CH₃ | H | H | F | CH(CH₃)C≡CH | S | |
| H | CH₃ | H | H | F | CH₂CH=CH₂ | S | |
| H | CH₃ | H | H | F | CH₂OCH₃ | S | |
| H | CH₃ | H | H | F | CH₂OCH₂CH₃ | S | |
| H | CH₃ | H | H | F | CH₂CH₂CH₃ | S | |
| H | CH₃ | H | H | F | CH(CH₃)₂ | S | |
| H | CH₃ | H | H | F | CH₂CH=CHCH₃ | S | |
| H | CH₃ | H | H | F | CH(CH₃)CH₂CH₃ | S | |
| H | CH₃ | H | H | F | CHF₂ | S | |
| H | CH₃ | H | H | F | CF₂CHF₂ | S | |
| H | CH₃ | H | H | F | CF₂CHFCl | S | |
| H | CH₃ | H | H | F | CF₂CHFCF₃ | S | |
| H | CH₃ | H | H | F | CH₂C≡CH | O | |
| H | CH₃ | H | H | F | CH(CH₃)C≡CH | O | |
| H | CH₃ | H | H | F | CH(CH₃)₂ | O | |

TABLE 4-continued

| R¹ | R² | R³ | R⁴ | R⁵ | R¹⁰ | W | Melting point °C. |
|---|---|---|---|---|---|---|---|
| H | CH₃ | H | H | F | CH₂C≡CH | O | |
| H | CH₃ | H | H | Cl | CH(CH₃)C≡CH | O | |
| H | CH₃ | H | H | Cl | CH(CH₃)₂ | O | |
| H | CH₃ | CH₃ | CH₃ | Cl | CH₂C≡CH | S | |
| H | CF₃ | H | H | F | CH₂C≡CH | S | |
| H | H | CH₃ | CH₃ | F | CH₂C≡CH | S | |
| H | H | —(CH₂)₅— | — | F | CH₂C≡CH | S | |

TABLE 5

| R¹ | R² | R³ | R⁴ | R⁵ | R⁸ | R⁹ | R¹⁰ | W | Melting point °C. |
|---|---|---|---|---|---|---|---|---|---|
| H | H | H | H | H | H | H | CH₃ | O | |
| H | H | H | H | F | H | H | CH₃ | O | |
| H | H | H | H | F | H | H | CH₂C≡CH | O | 206–208 |
| H | H | H | H | F | H | H | CH(CH₃)C≡CH | O | |
| H | H | H | H | F | H | H | CH₂CH=CH₂ | O | |
| H | H | H | H | F | CH₃ | H | CH₂C≡CH | O | |
| H | CH₃ | H | H | H | H | H | CH₃ | O | |
| H | CH₃ | H | H | F | H | H | CH₃ | O | |
| H | CH₃ | H | H | F | H | H | C₂H₅ | O | |
| H | CH₃ | H | H | F | H | H | CH₂CH₂CH₃ | O | |
| H | CH₃ | H | H | F | H | H | CH₂CH≡CH | O | |
| H | CH₃ | H | H | F | H | H | CH₂CH≡CH | O | |
| H | CH₃ | H | H | F | H | H | CH(CH₃)C≡CH | O | |
| H | CH₃ | H | H | Cl | H | H | CH₂C≡CH | O | |
| H | CH₃ | H | H | Cl | H | H | CH(CH₃)C≡CH | O | |
| H | CH₃ | H | H | F | CH₃ | H | CH₂C≡CH | O | |
| H | CH₃ | H | H | F | CH₃ | H | CH(CH₃)C≡CH | O | |
| H | CH₃ | H | H | F | CH₃ | H | CH₂CH=CH₂ | O | |
| H | CH₃ | H | H | F | CH₃ | CH₃ | CH₂CH≡CH | O | |
| H | CH₃ | H | H | F | H | H | CH₂CH≡CH | S | |

TABLE 5-continued

| R¹ | R² | R³ | R⁴ | R⁵ | R⁸ | R⁹ | R¹⁰ | W | Melting point °C. |
|---|---|---|---|---|---|---|---|---|---|
| H | CH₃ | H | H | F | CH₃ | H | CH₂CH≡CH | S | |
| H | CH₃ | H | H | F | CH₃ | CH₃ | CH₂CH≡CH | S | |
| H | CH₃ | CH₃ | CH₃ | F | H | H | CH₂C≡CH | O | |
| H | CF₃ | H | H | F | H | H | CH₂C≡CH | O | |
| H | CF₃ | H | H | F | H | H | CH₂CH=CH₂ | O | |
| H | H | CH₃ | CH₃ | F | H | H | CH₂C≡CH | O | |
| H | H | H | H | F | H | H | CH₃ | S | |
| H | H | H | H | F | H | H | CH₂C≡CH | S | |
| H | H | H | H | F | H | H | CH₂CH=CH₂ | S | |
| H | CF₃ | H | H | F | H | H | CH₂C≡CH | S | |
| H | CH₃ | CH₃ | CH₃ | F | H | H | CH₂C≡CH | S | |

TABLE 6

| R¹ | R² | R³ | R⁴ | R⁵ | R⁸ | R⁹ | Melting point °C. |
|---|---|---|---|---|---|---|---|
| H | H | H | H | H | F | F | |
| H | H | H | H | F | F | F | |
| H | H | H | H | F | H | H | |
| H | CH₃ | H | H | H | F | F | |
| H | CH₃ | H | H | F | F | F | |
| H | CH₃ | H | H | F | H | H | |
| H | H | CH₃ | CH₃ | F | F | F | |
| H | CH₃ | CH₃ | CH₃ | H | F | F | |
| H | CH₃ | CH₃ | CH₃ | F | F | F | |
| H | CF₃ | H | H | H | F | F | |
| H | CF₃ | H | H | F | F | F | |
| H | CF₃ | CH₃ | CH₃ | H | F | F | |
| H | CF₃ | CH₃ | CH3 | F | F | F | |
| H | CH₂CH₃ | H | H | H | F | F | |
| H | CH₂CH₃ | H | H | F | F | F | |

TABLE 7

| R¹ | R² | R³ | R⁴ | R⁵ | R⁶ | R⁷ | R⁸ | Melting point °C. |
|---|---|---|---|---|---|---|---|---|
| H | H | CH₃ | H | H | H | CO₂CH₃ | H | |
| H | H | CH₃ | H | H | H | CO₂CH₃ | CH₃ | |
| H | H | CH₃ | H | H | H | CO₂C₂H₅ | CH₃ | |
| H | H | CH₃ | H | H | H | CO₂C₂H₅ | H | |
| H | H | CH₃ | H | H | H | CO₂(CH₂)₂CH₃ | CH₃ | |
| H | H | CH₃ | H | H | H | CO₂(CH₂)₂CH₃ | H | |
| H | H | CH₃ | H | H | H | CO₂(CH₂)₃CH₃ | CH₃ | |
| H | H | CH₃ | H | H | H | CO₂(CH₂)₃CH₃ | H | |
| H | H | CH₃ | H | H | Cl | CO₂CH₃ | CH₃ | |
| H | H | CH₃ | H | H | Cl | CO₂C₂H₅ | CH₃ | |
| H | H | CH₃ | H | H | Cl | CO₂(CH₂)₂CH₃ | CH₃ | |
| H | H | CH₃ | H | H | Cl | CO₂(CH₂)₃CH₃ | CH₃ | |
| H | H | CH₃ | H | F | Cl | CO₂CH₃ | CH₃ | |
| H | H | CH₃ | H | F | Cl | CO₂C₂H₅ | CH₃ | |
| H | H | CH₃ | H | F | Cl | CO₂(CH₂)₂CH₃ | CH₃ | |
| H | H | CH₃ | H | F | Cl | CO₂(CH₂)₃CH₃ | CH3 | |

Formulations

Suitable formulations containing compounds of the formula I can be prepared in the conventional manner, namely as powders, granules, pellets, solutions, suspensions, emulsions, wettable powders, emulsifiable concentrates, et cetera. A great many of these forms can be applied directly. Preparations capable of being sprayed may be diluted with suitable media and sprayed in quantities of between a few and several hundred liters per hectare. Highly concentrated preparations are used mainly as intermediate products for other formulations. The formulations contain, as a rough estimate, between 0.1 and 99% by weight of active substance(s) and at least one representative of the group a) of 0.1 to 20% of surface-active substances and b) of approximately 1 to 99.9% of solid or liquid diluents. More precisely, they contain these constituents in approximately the following quantities:

|  | % by weight | | |
| --- | --- | --- | --- |
|  | Active substance | Diluent | Surface-active substance |
| Wettable powder | 20–90 | 0–74 | 1–10 |
| Suspensions in oil, emulsions, solutions, (including emulsifiable concentrates) | 3–50 | 40–95 | 0–15 |
| Aqueous suspensions | 10–50 | 40–84 | 1–20 |
| Dusts | 1–25 | 70–99 | 0–5 |
| Granules and pellets | 0.1–95 | 5–99.9 | 0–15 |
| Highly concentrated preparations | 90–99 | 0–10 | 0–2 |

*Active substance plus at least one surface-active substance or one diluent = 100% by weight.

Lower or higher contents of active substances may of course be present, depending On the intended application and the physical properties. Higher quantitative proportions of surface-active substance: active substance are sometimes desirable and are achieved by incorporation in the formulation or by mixing in the container.

Typical solid diluents are described in Watkins et al., "Handbook of Insecticide Dust Diluents and Carriers", 2nd Ed., Dorland Books, Caldwell, N.J. However other solids, either obtained by mining or prepared industrially, may be used. The better absorbing diluents are preferred for wettable powders and the denser diluents are preferred for dusts. Typical liquid diluents and solvents are described in Marsden, "Solvents Guide", 2nd Ed., Interscience, New York, 1950. For concentrated suspensions less than 0.1% are preferred. Concentrated solutions are preferably stable against phase separation at 0° C. Lists of surface-active substances and their recommended applications are contained in "McCutcheon's Detergents and Emulsifiers Annual", MC Publishing Corp., Ridgewood, N.J., as well as in Sisely and Wood "Encyclopedia of Surface Active Agents", Chemical Publishing Co. Inc., New York, 1964. All formulations may contain smaller quantities of additives to reduce foaming, agglomeration, corrosion, the growth of microorganisms, et cetera.

The methods for the preparation of these preparations are well-known. Solutions are prepared simply by mixing the components. Finely powdered solid preparations are obtained by mixing and, conventionally, by grinding, for example in a hammer mill or jet mill. Suspensions are obtained by wet grinding (see, for example, Littler, U.S. Pat. No. 3,060,084). Granules and pellets can be prepared by spraying the active substance on a preformed granule-shaped carrier or by agglomeration. In this connection see J. E. Browning, "Agglomeration", Chemical Engineering, Dec. 4, 1967, pages 147 ff. and "Perry's Chemical Engineer's Handbook", 5th Ed., McGraw-Hill, New York, 1973; pages 8–57 ff.

For further information regarding techniques of formulation reference may be made, for example, to the following:

H. M. Loux, U.S. Pat. No. 3,235,361, 15 February, 1966, column 6, line 16 to column 7, line 19 and examples 10 to 41;

R. W. Luckenbaugh, U.S. Pat. No. 3,309,192, 14 Mar., 1967, column 5, line 43 to column 7, line 62 and examples 8, 12, 15, 39, 41, 52, 53, 58, 132, 138–140, 162–164, 166, 167 and 169–182;

H. Gysin and E. Knusli, U.S. Pat. No. 2,891,855, 23 Jun., 1959, column 3, line 66 to column 5, line 17 and examples 1–4;

G. C. Klingman, "Weed Control as a Science", John Wiley and Sons Inc., New York, 1961, pages 81–96 and J. D. Fryer and S. A. Evans, "Weed Control Handbook", 5th Ed., Blackwell Scientific Publications, Oxford, 1968, pages 101–103.

In the following examples parts are by weight, unless specified otherwise.

Example A

| Wettable powder | |
| --- | --- |
| 7-(4-chlorophenyl)-5,5-dimethyl-6,8-dioxo-4-oxa-1,7-diazabicyclo[3.3.0]octane | 80% |
| Sodium alkylnaphthalensulphonate | 2% |
| Sodium lignosulphonate | 2% |
| Synthetic amorphous silicic acid | 3% |
| Kaolinite | 13% |

The constituents are mixed and ground in a hammer mill until all the solids have on the whole a particle size of less than 50 µm; subsequently they are mixed again and packed.

Example B

| Wettable powder | |
| --- | --- |
| 7-(4-chlorophenyl)-5,5-dimethyl-6,8-dioxo-4-oxa-1,7-diazabicyclo[3.3.0]octane | 50% |
| Sodium alkylnaphthalensulphonate | 2% |
| Methyl cellulose of low viscosity | 2% |
| Diatomaceous earth | 46% |

The constituents are mixed, coarsely ground in a hammer mill and then ground in a jet mill until virtually all the particles have a diameter of less than 10 µm. The product is mixed again prior to packing.

Example C

| Granular material | |
| --- | --- |
| Wettable powder from Example B | 5% |
| Attapulgite granules (USS 20–40 mesh; 0.84–0.42 mm) | 95% |

A suspension of wettable powder with 25% of solid substances is sprayed into a double-cone blender; the granules are then dried and packed.

Example D

| Extruded pellets | |
|---|---|
| 7-(4-chlorophenyl)-5,5-dimethyl-6,8-dioxo-4-oxa-1,7-diazabicyclo[3.3.0]octane | 25% |
| Anhydrous sodium sulphate | 10% |
| Crude calcium lignosulphonate | 5% |
| Sodium alkylnaphthalensulphonate | 1% |
| Calcium/magnesium bentonite | 59% |

The constituents are mixed, ground in a hammer mill and then wetted with approximately 12% water. The mixture is extruded into cylinders having a diameter of approximately 3 mm, which are cut into pellets of approximately 3 mm in length. The latter can be used directly after drying; the dried pellets may however be comminuted so that they pass through the USS No. 20 sieve (apertures 0.84 mm diameter). The granules remaining behind on the sieve USS No. 40 (0.42 mm diameter aperture) may be packed for use, while the fine portions are recycled.

Example E

| Granular material of low strength | |
|---|---|
| 7-(4-chlorophenyl)-5,5-dimethyl-6,8-dioxo-4-oxa-1,7-diazabicyclo[3.3.0]octane | 1% |
| N,N-dimethylformamide | 9% |
| Attapulgite granules (USS sieve 20 to 40) | 90% |

The active substance is dissolved in the solvent and the solution is sprayed onto dust-free granules in a double-cone blender. After spraying the solution, the mixer is allowed to continue running for a short period, after which the granules are packed.

Example F

| Granular material | |
|---|---|
| 7-(4-chlorophenyl)-5,5-dimethyl-6,8-dioxo-4-oxa-1,7-diazabicyclo[3.3.0]octane | 80% |
| Wetting agent | 1% |
| Crude lignosulphonate (with 5 to 20% of the natural sugar) | 10% |
| Attapulgite-clay | 9% |

The constituents are mixed and ground until they pass through an 100 mesh sieve. This material is then delivered to a fluid bed granulator, where the air current is adjusted so that the material is easily whirled up, with a fine jet of water being sprayed onto the whirled material. Fluidisation and spraying are continued until granules of the desired size are obtained. Spraying is then discontinued but fluidisation, optionally with the addition of heat, is continued until the water content has fallen to the desired value, generally less than 1%. The material is then removed and the desired particle size range, normally from 14 to 100 mesh (from 1410 to 149 μm) is screened out, after which it is packed for use.

Example G

| Aqueous suspension | |
|---|---|
| 7-(4-chlorophenyl)-5,5-dimethyl-6,8-dioxo-4-oxa-1,7-diazabicyclo[3.3.0]octane | 40% |
| Thickener based on polyacrylic acid | 0.3% |
| Dodecylphenol polyethylene glycol ether | 0.5% |
| Disodium phosphate | 1% |
| Monosodium phosphate | 0.5% |
| Polyvinyl alcohol | 1.0% |
| Water | 56.7% |

The components are mixed and ground together in a sand mill in order to obtain particles having on the whole a size of less than 5 μm.

Example H

| Strong concentrate | |
|---|---|
| 7-(4-chlorophenyl)-5,5-dimethyl-6,8-dioxo-4-oxa-1,7-diazabicyclo[3.3.0]octane | 99% |
| Silicic acid aerogel | 0.5% |
| Synthetic amorphous silicic acid | 0.5% |

The constituents are mixed and ground in a hammer mill in order to obtain a material that passes through a USS-sieve No. 50 (0.3 mm aperture). The concentrate may, if required, contain other constituents.

Example I

| Wettable powder | |
|---|---|
| 7-(4-chlorophenyl)-5,5-dimethyl-6,8-dioxo-4-oxa-1,7-diazabicyclo[3.3.0]octane | 90.0% |
| Dioctyl sodium sulphosuccinate | 0.1% |
| Synthetic fine silicic acid | 9.9% |

The constituents are mixed and ground in a hammer mill in order to obtain particles having on the whole a size of less than 100 μm. The material is screened through a USS No. 50 sieve and then packed.

Example J

| Wettable powder | |
|---|---|
| 7-(4-chlorophenyl)-5,5-dimethyl-6,8-dioxo-4-oxa-1,7-diazabicyclo[3.3.0]octane | 40% |
| Sodium lignosulphonate | 20% |
| Montmorillonite clay | 40% |

The constituents are thoroughly mixed, coarsely ground in a hammer mill and then ground in an air jet mill in order to obtain particles having on the whole a size of less than 10 μm. The material is mixed again and then packed.

Example K

| Suspension in oil | |
|---|---|
| 7-(4-chlorophenyl)-5,5-dimethyl-6,8-dioxo-4-oxa-1,7-diazabicyclo[3.3.0]octane | 35% |
| Mixture of polyalcohol carboxylic acid esters and oil-soluble petroleum sulphonates | 6% |
| Xylene | 59% |

The components are mixed and ground together in a sand mill in order to obtain particles having on the whole a size of less than 5 µm. The product may be used directly, diluted with oil or emulsified in water.

Example L

| Dust | |
|---|---|
| 7-(4-chlorophenyl)-5,5-dimethyl-6,8-dioxo-4-oxa-1,7-diazabicyclo[3.3.0]octane | 10% |
| Attapulgite | 10% |
| Pyrophyllite | 80% |

The active substance is mixed with attapulgite and then passed through a hammer mill in order to obtain particles on the whole of less than 200 µm. The ground concentrate is then mixed with powdered pyrophyllite until homogeneous.

Example M

| Suspension in oil | |
|---|---|
| 7-(4-chlorophenyl)-5,5-dimethyl-6,8-dioxo-4-oxa-1,7-diazabicyclo[3.3.0]octane | 25% |
| Polyoxyethylene sorbitol hexaoleate | 5% |
| Highly aliphatic hydrocarbon oil | 70% |

The constituents are ground together in a sand mill until the particle size of the solids is less than approximately 5 µm. The resulting thick suspension may be used directly, but it is preferably used after dilution with oils or after emulsification in water.

BIOLOGICAL EXAMPLES

Experimental results show that the compounds according to the present invention are effective herbicides. They are suitable for the broad-spectrum control of weeds prior to and after the germination thereof on surfaces where the entire vegetation is to be kept under control, for example in the vicinity of industrial storage spaces, parking spaces, drive-in cinemas, around advertising hoardings, along country roads and along railways. Many of the compounds are also suitable for selective weed control in the cultivation of rice, wheat, barley, maize, soya beans, sugar beet and cotton.

The quantity to be applied of the compounds according to the present invention is dependent on numerous factors, including use as selective or as universal herbicides, the respective field crops, the nature of the weeds to be controlled, weather and climate, the formulation selected, the method of application, the quantity of foliage plants et cetera. In general the compounds should be applied in quantities of between 0.001 and 20 kg/ha, with the lower quantities being suitable for lighter soils and/or soils with a low content of organic substances or for instances where only a short reaction period is required, for example in the case of herbicides for fallow land.

The compounds according to the present invention may be used in combination with any other commercially available herbicides.

The herbicidal properties of the compounds according to the present invention were detected in a series of greenhouse experiments. The test methods and results are given below.

Biological tables

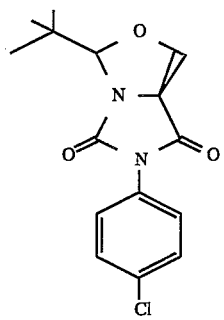

Compound 1

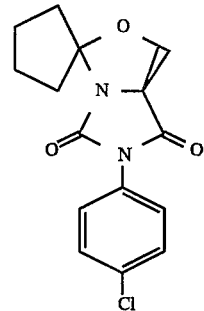

Compound 2

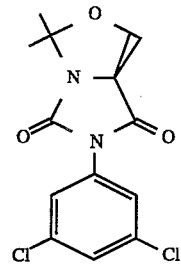

Compound 3

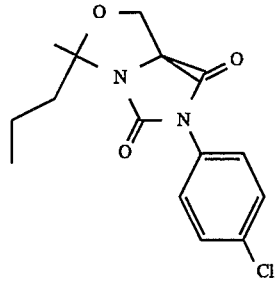

Compound 4

29
-continued
Biological tables
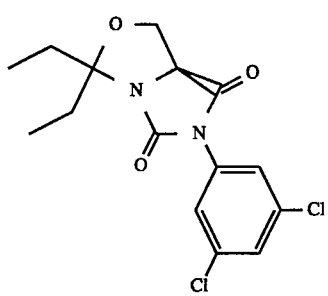
Compound 5
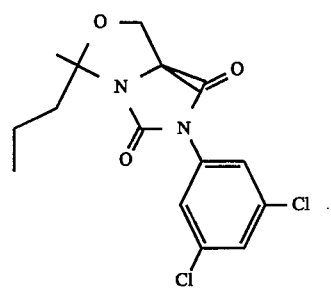
Compound 6
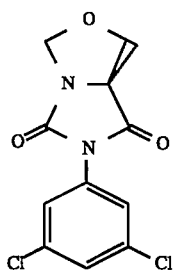
Compound 7
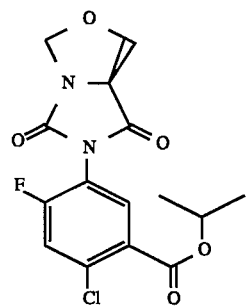
Compound 8
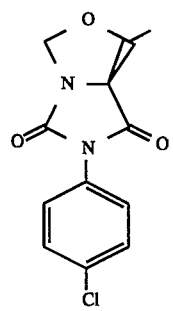
Compound 9
30
-continued
Biological tables
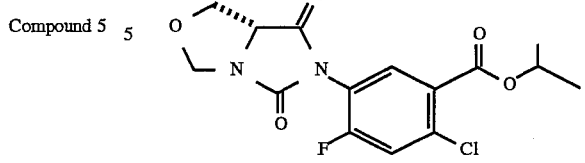
Compound 10
Compound 11
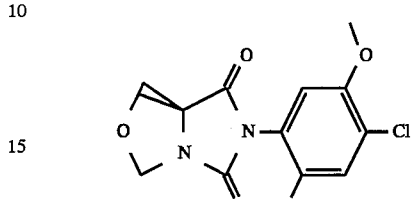
Compound 12
Compound 13
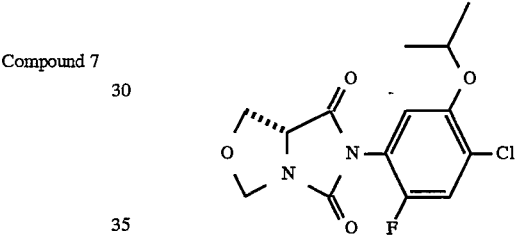
Compound 14
Compound 15
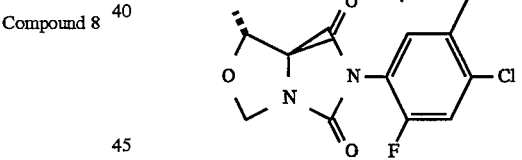
Compound 16
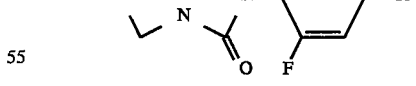

-continued
Biological tables

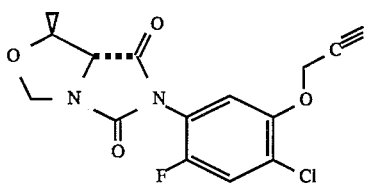

Compound 17

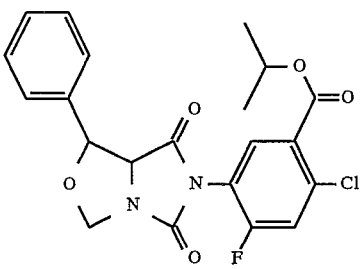

Compound 18

Test methods

Seeds of Digitaria spp., Echinochloa crus-galli, Setaria feberii, Arena fatua, Bromus secalinus, Abutilon theophrasti, Ipomoea spp., Xanthium pensylvanicum and sorghum tubers were sown and prior to germination were treated with the test chemicals dissolved in a non-phytotoxic solvent.

In addition these weed species were treated with a preparation intended for soils and foliage. At the time of treatment the plants were between 2 and 18 cm in height. The treated plants and the control plants were maintained in the greenhouse for 16 d, after which all samples were compared with the control plants and the effect of the treatment was assessed visually. The assessments summarised in Table A are on a numerical scale from 0=without damage to 10=complete annihilation.

The descriptive symbols shown have the following meanings:

C=chlorosis/necrosis
B=burning
H=effect on development
E=retardation of germination
G=promotion of growth

TABLE A

Application after germination (dosage 2 kg of active substance/ha)

| | Cpd. 1 | Cpd. 2 | Cpd. 3 | Cpd. 4 | Cpd. 5 | Cpd. 6 | Cpd. 7 | Cpd. 8 | Cpd. 9 | Cpd. 10 | Cpd. 11 | Cpd. 12 | Cpd. 13 | Cpd. 14 | Cpd. 15 | Cpd. 16 | Cpd. 17 | Cpd 18 |
|---|---|---|---|---|---|---|---|---|---|---|---|---|---|---|---|---|---|---|
| Echinocloa c.-g. | 2B | 2B | 1B | 1B | 1B | 1B | 2B | 7B | 2B | 10B | 2B | 9B | 10B | 9B | 10B | 9 | 10 | 3 |
| Bromus secalinus | 1B | 1B | 0 | 0 | 0 | 0 | 1B | 2B | 1B | 10B | 1B | 5B | 9B | 9B | 10B | — | — | — |
| Xanthium pens. | 1B | 1B | 0 | 0 | 0 | 2B | 0 | 1B | 1B | — | — | — | — | — | — | — | — | — |
| Ipomoea spp. | 4B | 6B | 0 | 7G, 2C | 3G, 1B | 5G, 2C | 0 | 8B | 6B | 10B | 8B | 10B | 10B | 10B | 10B | 10 | 10 | 10 |
| Sorghum | 2B | 2B | 1B | 1B | 0 | 1B | 1B | 3B | 2B | 10B | 3B | 8B | 9B | 4B | 10B | 10 | 10 | 8 |
| Setaria feberii | 1B | 1B | 0 | 1B | 0 | 1B | 1B | 7B | 1B | 10B | 3B | 9B | 10B | 10B | 10B | 10 | 10 | 6 |
| Digitaria spp. | 1B | 1B | 1B | 1B | 1B | 1B | 1B | 7B | 2B | 10B | 3B | 9B, 6H | 10B | 9B | 10B | 10 | 10 | 7 |
| Abutilon th. | 2B | 1B | 0 | 0 | 0 | 5B | 1B | 8B | 7B | 10B | 4B | 10B | 10B | 10B | 10B | 10 | 10 | 6 |
| Avena fatua | 2B | 2B | 0 | 1B | 1B | 1B | 1B | 3B | 2B | 10B | 2B | 6B | 9B | 9B | 10B | 10 | 10 | 7 |

TABLE B

Application prior to germination (dosage 2 kg of active substance/ha)

| | Cpd. 1 | Cpd. 2 | Cpd. 3 | Cpd. 4 | Cpd. 5 | Cpd. 6 | Cpd. 7 | Cpd. 8 | Cpd. 9 | Cpd. 10 | Cpd. 11 | Cpd. 12 | Cpd. 13 | Cpd. 14 | Cpd. 15 | Cpd. 16 | Cpd. 17 | Cpd. 18 |
|---|---|---|---|---|---|---|---|---|---|---|---|---|---|---|---|---|---|---|
| Echincloa c.-g. | 0 | 0 | 0 | 0 | 0 | 0 | 0 | 6H | 0 | 9C | 4C | 9C | 10C | 9C | 10C | — | — | — |
| Bromus secalinus | 0 | 0 | 0 | 0 | 0 | 0 | 0 | 2G | 1C | 9C | 3C | 8C | 9C | 9C | 10C | — | — | — |
| Xanthium pens. | 0 | 0 | 0 | 0 | 0 | 0 | 0 | 2G | 0 | — | — | — | — | — | — | — | — | — |
| Ipomoea spp. | 0 | 0 | 0 | 0 | 2G | 0 | 0 | 0 | 1C | 10C | 4C | 10C | 9C | 10C | 10C | 10 | 10 | 9 |
| Sorghum | 0 | 0 | 0 | 0 | 0 | 0 | 0 | 0 | 1C | 10C | 2C | 10C | 9C | 8C | 10C | 10 | 10 | 7 |
| Setaria feberii | 0 | 0 | 0 | 0 | 0 | 0 | 0 | 9H | 0 | 10C | 7C, 3H | 10C | 10C | 10C | 10C | 10 | 10 | 9 |
| Digitaria spp. | 0 | 0 | 0 | 0 | 0 | 0 | 0 | 9H | 1C | 10C | 6C | 9C | 9C | 10C | 10C | 10 | 10 | 7 |
| Abutilon th. | 0 | 0 | 0 | 0 | 0 | 0 | 0 | 10C | 1C | 10C | 10C | 10C | 10C | 10C | 10C | 10 | 10 | 7 |
| Avena fatua | 0 | 0 | 0 | 0 | 0 | 0 | 0 | 0 | 1C | 9C | 1C | 9C | 9C | 8C | 10C | 10 | 10 | 3 |

TABLE C

Application after germination (dosage 0.2 kg/ha)

| Object | Cpd. 10 | Cpd. 12 | Cpd. 13 | Cpd. 15 | Cpd. 16 | Cpd. 17 |
|---|---|---|---|---|---|---|
| Maize | 9B | 2B | 2B | 6B | 5B | 5B |
| Wheat | 4B | 2B | 3B | 7B | 5B | 7B |
| Echinocloa c.-g. | 9B | 3B | 9B | 10B | 8B | 9B |
| Xanthium pens. | 7B | — | — | — | 6B | 4B |
| Ipomoea spp. | 10B | 8B | 9B | 19B | 8B | 8B |
| Sorghum | 4B | 2B | 3B | 7B | 7B | 7B |
| Setaria feberii | 7B | 4B | 6B | 10B | 8B | 9B |
| Digitaria spp. | 3B | 2B | 3B | 9B | 8B | 7B |
| Abutilon th. | 10B | 9B | 9B | 10B | 9B | 10B |
| Avena fatua | 3B | 2B | 3B | 7B | 5B | 5B |

TABLE D

Application prior to germination (dosage 0.2 kg/ha)

| Object | Cpd. 10 | Cpd. 12 | Cpd. 13 | Cpd. 15 | Cpd. 16 | Cpd. 17 |
|---|---|---|---|---|---|---|
| Maize | 1C | 0 | 0 | 2C | 6H | 6H |
| Wheat | 0 | 0 | 2G | 1G | 2C | 2C |
| Echinocloa c.-g. | 1C | 1C | 6C | 10C | 9H | 9H |
| Xanthium pens. | 7B | — | — | — | 2H | 0 |
| Ipomoea spp. | 3C | 1C | 7C | 10C | 5H | 10E |
| Sorghum | 1C | 0 | 2C | 4C | 8H | 5G |
| Setaria feberii | 9C | 6C | 7C | 10C | 10H | 10H |
| Digitaria spp. | 9G | 3C | 4C | 10C | 10H | 10H |
| Abutilon th. | 10C | 10C | 10C | 10C | 10C | 10C |
| Avena fatua | 2C | 1C | 0 | 4C | 7H | 7H |

We claim:

1. An anellated (oxa) hydantoin of the formula I,

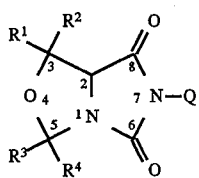

wherein $R^1$ and $R^2$, independently of one another, represent hydrogen or a radical selected from the group consisting of $(C_1-C_4)$ alkyl, $(C_1-C_2)$ haloalkyl or phenyl optionally fluorine-substituted, $R^3$ and $R^4$, independently of one another, represent hydrogen, $(C_1-C_4)$ alkyl, phenyl, both optionally fluorine- and/or chlorine-, bromine- or methyl-substituted, or $(C_1-C_4)$ alkoxy; or also together form a carbocyclic ring which may optionally be $(C_1-C_4)$ alkyl-substituted, Q represents one of the radicals $Q_{-1}$, $Q_{-2}$, $Q_{-3}$, $Q_{-4}$, $Q_{-5}$, $Q_{-6}$, $Q_{-7}$

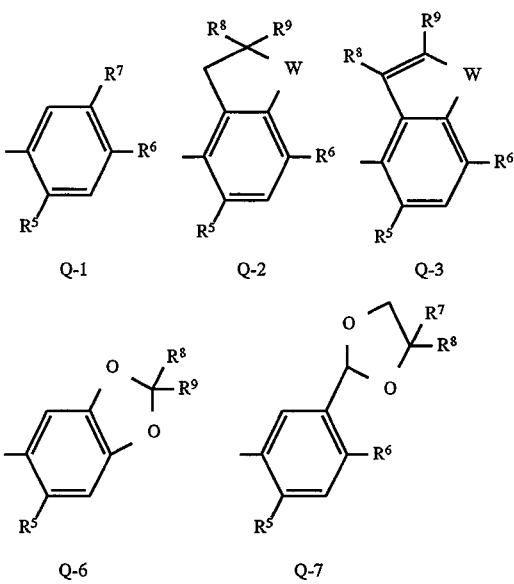

wherein

W represents O or S, $R^5$ represents hydrogen or halogen, $R^6$ represents $(C_1-C_2)$ alkyl, $(C_1-C_2)$ haloalkyl, $OCH_3$, $SCH_3$, $OCHF_2$, halogen, CN or $NO_2$, $R^7$ represents hydrogen, $(C_1-C_8)$ alkyl, $(C_1-C_8)$ haloalkyl, halogen, $OR^{11}$, $S(O)_n R^{11}$, $COR^{11}$, $COR^{11}$, $CO_2R^{11}$, $C(O)SR^{11}$, $C(O)NR^{12}R^{13}$, CHO, $CH=CHCO_2R^{11}$, $CO_2N=CR^{14}R^{15}$, $NO_2$, CN, $NHSO_2R^{16}$ or $NHSO_2NHR^{16}$, $R^8$ represents hydrogen, $(C_1-C_3)$ alkyl, $(C_1-C_3)$ haloalkyl or halogen, $R^9$ represents hydrogen, $(C_1-C_3)$ alkyl, $(C_1-C_3)$ haloalkyl or halogen; or if Q is Q-2 or Q-6, $R^8$ and $R^9$ together with the carbon atom to which they are bonded can be C=O;

$R^{11}$ represents $(C_1-C_8)$ alkyl, $(C_3-C_8)$ cycloalkyl, $(C_3-C_8)$ alkenyl, $(C_3-C_8)$ alkynyl, $(C_1-C_8)$ haloalkyl, $(C_2-C_8)$ alkoxyalkyl, $(C_2-C_8)$ alkylthioalkyl, $(C_2-C_8)$ alkylsulphinylalkyl, $(C_2-C_8)$ alkylsulphonylalkyl, $(C_3-C_8)$ alkoxyalkoxyalkyl, $(C_4-C_8)$ cycloalkylalkyl, $(C_2-C_4)$ carboxyalkyl, $(C_3-C_8)$ alkoxycarbonylalkyl, $(C_6-C_8)$ alkynyloxycarbonylalkyl, $(C_4-C_8)$ alkenoxyalkyl, $(C_6-C_8)$ cycloalkoxyalkyl, $(C_4-C_8)$ alkynyloxyalkyl, $(C_3-C_8)$ haloalkoxyalkyl, $(C_4-C_8)$ haloalkenyloxyalkyl, $(C_4-C_8)$ haloalkynyloxyalkyl, $(C_6-C_8)$ cycloalkylthioalkyl, $(C_4-C_8)$ alkenylthioalkyl, $(C_4-C_8)$ alkynylthioalkyl, $(C_1-C_4)$ alkyl-substituted with phenoxy or benzyloxy, Which may both optionally be halogen-, $(C_1-C_8)$ alkyl- or $(C_1-C_8)$ haloalkyl-substituted; $(C_4-C_8)$ trialkylsilylalkyl, $(C_3-C_8)$ cyanoalkyl, $(C_3-C_8)$ halocycloalkyl, $(C_3-C_8)$ haloalkenyl, $(C_5-C_8)$ alkoxyalkenyl, $(C_5-C_8)$ haloalkoxyalkenyl, $(C_5-C_8)$ alkylthioalkenyl, $(C_3-C_8)$ haloalkynyl, $(C_5-C_8)$ alkoxyalkynyl, $(C_8-C_8)$ haloalkoxyalkynyl, $(C_5-C_8)$ alkylthioalkynyl, $(C_2-C_8)$ alkylcarbonyl, benzyl optionally substituted with halogen, $(C_1-C_3)$ alkyl or $(C_1-C_3)$ haloalkyl; $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl, both optionally substituted with halogen, $(C_1-C_3)$ alkyl, $(C_1-C_3)$ haloalkyl or $(C_1-C_4)$ alkoxy, $R^{12}$ and $R^{14}$, independently of one another, represent hydrogen or $(C_1-C_4)$ alkyl, $R^{13}$ and $R^{15}$, independently of one another, represent $(C_1-C_4)$ alkyl, phenyl, optionally substituted with halogen, $(C_1-C_3)$ alkyl, $(C_1-C_3)$ haloalkyl or $(C_1-C_4)$ alkoxy, $R^{14}$ and $R^{15}$ together with the carbon atom to which they are bonded can form a $(C_3-C_8)$ cycloalkyl group, $R^{16}$ represents $(C_1-C_4)$ alkyl or $(C_1-C_4)$ haloalkyl, $R^{17}$ represents hydrogen or $(C_1-C_3)$ alkyl, $R^{18}$ represents $(C_1-C_6)$ alkyl, $(C_3-C_6)$ alkenyl or $(C_3-C_6)$ alkynyl, and n represents 0, 1, 2.

2. The anellated (oxa) hydantoin of the formula I according to claim 1, characterised in that at least one of the radicals $R^1$ and $R^2$, independently of one another, represent hydrogen or a group selected from the group consisting of $(C_1-C_4)$ alkyl, $(C_1-C_2)$ haloalkyl or phenyl, which is optionally fluorine-substituted, $R^3$ and $R^4$, independently of one another, represent hydrogen, $(C_1-C_3)$ alkyl, phenyl, optionally fluorine-substituted and/or chlorine-, bromine- or methyl-substituted, $(C_1-C_2)$ alkoxy; or together form a carbocyclic ring which may optionally be $(C_1-C_2)$ alkyl-substituted, W represents O or S, n represents 0, 1, 2, $R^5$ represents hydrogen or halogen, $R^6$ represents halogen or CN, $R^7$ represents hydrogen, $(C_1-C_4)$ alkyl, $(C_1-C_4)$ haloalkyl halogen, $OR^{11}$, $S(O)_nR^{11}$, $COR^{11}$, $CO_2R^{11}$, $C(O)SR^{11}$, $C(O)NR^{12}R^{13}$, $CH=CHCO_2R^{11}$, $CO_2N=CR^{14}R^{15}$, $NHSO_2R^{16}$ or $NHSO_2NHR^{16}$, $R^8$ represents hydrogen, $(C_1-C_3)$ alkyl or $(C_1-C_3)$ haloalkyl, $R^9$ represents hydrogen, $(C_1-C_3)$ alkyl or $(C_1-C_3)$ haloalkyl; or if Q is Q-2 or Q-6, $R^8$ and $R^9$ together with the carbon atom to which they are bonded can be C=O;

$R^{11}$ represents $(C_1-C_4)$ alkyl, $(C_3-C_6)$ cycloalkyl, $(C_3-C_6)$ alkenyl, $(C_3\ C_6)$ alkynyl, $(C_1-C_4)$ haloalkyl, $(C_2-C_4)$ alkoxyalkyl, $(C_2-C_4)$ alkylthioalkyl, $(C_2-C_4)$ alkylsulphinylalkyl, $(C_2-C_4)$ alkylsulphonylalkyl, $(C_3-C_6)$ alkoxyalkoxyalkyl, $(C_4-C_8)$ cycloalkylalkyl, $(C_2-C_4)$ carboxyalkyl, $(C_3-C_6)$ alkoxycarbonylalkyl, $(C_6-C_8)$ alkenyloxycarbonylalkyl, $(C_6-C_8)$ alkynyloxycarbonylalkyl, $(C_4-C_6)$ alkenoxyalkyl, $(C_6-C_8)$ cycloalkoxyalkyl, $(C_4-C_6)$ alkynyloxyalkyl, $(C_3-C_6)$ haloalkoxyalkyl, $(C_4-C_8)$ haloalkenyloxyalkyl, $(C_4-C_6)$ haloalkynyloxyalkyl, $(C_6-C_8)$ cycloalkylthioalkyl, $(C_4-C_6)$ alkenylthioalkyl, $(C_4-C_6)$ alkynylthioalkyl, $(C_1-C_2)$ alkyl-substituted with phenoxy or benzyloxy, which may both optionally be halogen-, $(C_1-C_3)$ alkyl- or $(C_1-C_3)$ haloalkyl-substituted; $(C_4-C_8)$ trialkylsilylalkyl, $(C_3-C_4)$ cyanoalkyl, $(C_3-C_6)$ halocycloalkyl, $(C_3-C_6)$ haloalkenyl, $(C_5-C_6)$ haloalkoxyalkenyl, $(C_5-C_6)$ alkylthioalkenyl, $(C_3-C_6)$ haloalkynyl, $(C_5-C_6)$ alkoxyalkynyl, $(C_5-C_6)$ haloalkoxyalkynyl, $(C_5-C_6)$ alkylthioalkynyl, $(C_2-C_4)$ alkylcarbonyl, benzyl optionally substituted with halogen, $(C_1-C_2)$ alkyl or $(C_1-C_2)$ haloalkyl; $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl, both optionally substituted with halogen, $(C_1-C_3)$ alkyl, $(C_1-C_3)$ haloalkyl or $(C_1-C_4)$ alkoxy, $R^{12}$ and $R^{14}$, independently of one another, represent hydrogen or $(C_1\ C_2)$ alkyl, $R^{13}$ and $R^{15}$, independently of one another, represent $(C_1-C_2)$ alkyl, phenyl, optionally substituted with halogen, $(C_1-C_2)$ alkyl, $(C_1-C_2)$ haloalkyl or $(C_1-C_2)$ alkoxy, $R^{14}$ and $R^{15}$ together with the carbon atom to which they are bonded can form a $(C_3-C_6)$ cycloalkyl group, $R^{16}$ represents $(C_1-C_4)$ alkyl or $(C_1-C_4)$ haloalkyl, $R^{17}$ represents hydrogen or $(C_1-C_3)$ alkyl, $R^{18}$ represents $(C_1-C_4)$ alkyl, $(C_3-C_4)$ alkenyl or $(C_3-C_4)$ alkynyl.

3. The anellated (oxa) hydantoin of the formula I according to claim 1, characterised in that at least one of the radicals $R^1$ and $R^2$, independently of one another, represent hydrogen or a radical selected from the group consisting of $(C_1-C_3)$ alkyl, $(C_1-C_2)$ haloalkyl or phenyl, which is optionally fluorine-substituted, $R^3$ and $R^4$, independently of one another, represent hydrogen, $(C_1-C_3)$ alkyl, or also together form a 5- to 6-membered carbocyclic ring, which may optionally substituted with $(C_1-C_4)$ alkyl radicals, W represents O or S, n represents 0, 1, or 2, $R^5$ represents hydrogen, fluorine or chlorine, $R^6$ represents chlorine, bromine or cyanogen, $R^7$ represents hydrogen, $OR^{11}$ or $CO_2R^{11}$, $R^8$ and $R^9$, independently of one another, represent hydrogen, $(C_1-C_2)$ alkyl or $(C_1-C_2)$ haloalkyl, $R^{11}$ represents $(C_1-C_4)$ alkyl, $(C_3-C_6)$ cycloalkyl, $(C_3-C_6)$ alkenyl, $(C_3\ C_6)$ alkynyl, $(C_1-C_4)$ haloalkyl, $(C_2-C_4)$ alkoxyalkyl, $(C_2-C_4)$ alkylthioalkyl, $(C_2-C_4)$ alkylsulphinylalkyl, $(C_2-C_4)$ alkylsulphonylalkyl, $(C_3-C_6)$ alkoxyalkoxyalkyl, $(C_4-C_8)$ cycloalkylalkyl, $(C_2-C_4)$ carboxyalkyl, $(C_3-C_6)$ alkoxycarbonylalkyl, $(C_6-C_8)$ alkenyloxycarbonylalkyl, $(C_6-C_8)$ alkynyloxycarbonylalkyl, $(C_6-C_8)$ cycloalkoxyalkyl, $(C_4-C_6)$ alkenyloxyalkyl, $(C_4-C_6)$ alkynyloxyalkyl, $(C_3-C_6)$ haloalkoxyalkyl, $(C_4-C_8)$ haloalkenyloxyalkyl, $(C_4-C_6)$ haloalkynyloxyalkyl, $(C_6-C_8)$ cycloalkylthioalkyl, $(C_4-C_6)$ alkenylthioalkyl, $(C_4-C_8)$ alkynylthioalkyl, $(C_1-C_2)$ alkyl-substituted with phenoxy or benzyloxy, which are both optionally substituted with halogen-, $(C_1-C_3)$ alkyl- or $(C_1-C_3)$ haloalkyl; $(C_4-C_8)$ trialkylsilylalkyl, $(C_3-C_4)$ cyanoalkyl, $(C_3-C_6)$ halocycloalkyl, $(C_3-C_8)$ haloalkenyl, $(C_5-C_6)$ alkoxyalkenyl, $(C_5-C_6)$ haloalkoxyalkenyl, $(C_5-C_6)$ alkylthioalkenyl, $(C_3-C_6)$ haloalkynyl, $(C_5-C_6)$ alkoxyalkynyl, $(C_5-C_6)$ haloalkoxyalkynyl, $(C_5-C_6)$ alkylthioalkynyl, $(C_2-C_4)$ alkylcarbonyl, benzyl optionally substituted with halogen, $(C_1-C_2)$ alkyl or $(C_1-C_2)$ haloalkyl; $CHR^{17}COR^{18}$, $CHR^{17}P(O)(OR^{18})_2$, $P(O)(OR^{18})_2$, $CHR^{17}P(S)(OR^{18})_2$, $CHR^{17}C(O)NR^{12}R^{13}$, $CHR^{17}C(O)NH_2$, phenyl both optionally substituted with fluorine, chlorine or bromine, $(C_1-C_2)$ haloalkyl or $(C_1-C_2)$ alkoxy, $R^{12}$ represents hydrogen or $(C_1-C_2)$ alkyl, $R^{13}$ represents $(C_1-C_2)$ alkyl, phenyl optionally substituted with fluorine, chlorine, bromine, $(C_1-C_2)$ alkyl, ($C_1$–$C_2$) haloalkyl or ($C_1$ $C_2$) alkoxy, wherein one or more H atoms in each ring may be substituted optionally by ($C_1$–$C_2$) alkyl, $R^{17}$ represents hydrogen or ($C_1$–$C_2$) alkyl, $R^{18}$ represents ($C_1$ $C_2$) alkyl, ($C_3$–$C_4$) alkenyl or ($C_3$–$C_4$) alkynyl.

4. The anellated (oxa) hydantoin of the formula I according to claim 1, characterised in that at least one of the radicals $R^1$ and $R^2$, independently of one another, represent hydrogen, ($C_1$–$C_3$) alkyl, ($C_1$–$C_2$) haloalkyl or phenyl, $R^3$ and $R^4$, independently of one another, represent hydrogen, ($C_1$–$C_3$) alkyl, or also together form a 5- to 6-membered carbocyclic ring, $R^5$ represents fluorine or chlorine, $R^6$ represents chlorine, $R^7$ represents $OR^{11}$ or $CO_2R^{11}$, $R^{11}$ represents ($C_1$–$C_4$) alkyl, ($C_3$–$C_6$) cycloalkyl, ($C_3$–$C_6$) alkenyl, ($C_3$–$C_4$) alkynyl, ($C_1$–$C_3$) haloalkyl, ($C_2$–$C_4$) alkoxyalkyl, ($C_3$–$C_6$) alkoxycarbonylalkyl, ($C_6$–$C_8$) alkenyloxycarbonylalkyl or ($C_6$–$C_8$) alkynyloxycarbonylalkyl.

5. A herbicidal composition, characterised by having an effective content of a compound of the formula I according to claim 1 and a carrier for that.

6. A method for controlling noxious plants, characterised in that a herbicidally effective quantity of the compound according to claim 1 is applied to the noxious plants or to their environment.

* * * * *